US009310327B2

(12) United States Patent
Roper et al.

(10) Patent No.: US 9,310,327 B2
(45) Date of Patent: Apr. 12, 2016

(54) TOROIDAL CONDUCTIVITY PROBE WITH INTEGRATED CIRCUITRY

(75) Inventors: Brian Keith Roper, Phoenix, AZ (US); Todd Kenneth Roper, Glendale, AZ (US); Steve Lurcott, Scottsdale, AZ (US); Robert Trepp, Mesa, AZ (US)

(73) Assignee: SGS Instruments LLC, Tempe, AZ (US)

( * ) Notice: Subject to any disclaimer, the term of this patent is extended or adjusted under 35 U.S.C. 154(b) by 185 days.

(21) Appl. No.: 13/129,575

(22) PCT Filed: Feb. 26, 2010

(86) PCT No.: PCT/US2010/025651
§ 371 (c)(1),
(2), (4) Date: May 16, 2011

(87) PCT Pub. No.: WO2011/096946
PCT Pub. Date: Aug. 11, 2011

(65) Prior Publication Data
US 2012/0326711 A1 Dec. 27, 2012

Related U.S. Application Data

(60) Provisional application No. 61/302,122, filed on Feb. 6, 2010.

(51) Int. Cl.
*G01R 33/09* (2006.01)
*G01N 27/02* (2006.01)
*G01N 30/64* (2006.01)

(52) U.S. Cl.
CPC .......... *G01N 27/025* (2013.01); *G01N 27/023* (2013.01); *G01N 2030/645* (2013.01)

(58) Field of Classification Search
CPC .............. G01N 27/023; G01N 27/025; G01N 2030/645
See application file for complete search history.

(56) References Cited

U.S. PATENT DOCUMENTS

| 2,542,057 | A | * | 2/1951 | Relis | G01N 27/025 324/204 |
| 2,774,239 | A | * | 12/1956 | Fitzgerald | 73/575 |
| 5,157,332 | A | * | 10/1992 | Reese | 324/445 |
| 6,586,939 | B1 | * | 7/2003 | Fanini et al. | 324/339 |
| 7,275,420 | B2 | * | 10/2007 | Discenzo | 73/54.28 |
| 7,965,167 | B2 | * | 6/2011 | Volker | G01N 27/025 324/445 |
| 8,633,703 | B2 | * | 1/2014 | Eberheim et al. | 324/445 |
| 2005/0179439 | A1 | * | 8/2005 | Talutis | G01N 27/023 324/445 |

(Continued)

*Primary Examiner* — Tung X Nguyen
*Assistant Examiner* — Adam Clarke
(74) *Attorney, Agent, or Firm* — Gregory Stauf

(57) ABSTRACT

An apparatus and process for making noncontact measurements of liquid conductivity are disclosed. This apparatus forms a conductivity cell and uses two toroids, one to generate a magnetic field and another to sense the magnetic field, placed in an enclosure which allows liquid to pass through it for measurement. Ground planes constructed preferably of printed circuit boards with conductive layers are used to reduce capacitive coupling between the toroids and provide better shielding. Circuitry on or near these circuit boards are used to convert local, low level signals from a sensing toroid to signals which can be more readily passed to and from a recording system or operator without degradation. Sensors on or near these circuit boards can be used to sense environmental conditions in order to improve operation and stability of the conductivity cell. Methods and apparatus for increasing circuit sensitivity and calibrating the sensor are also disclosed.

41 Claims, 7 Drawing Sheets

(56) References Cited

U.S. PATENT DOCUMENTS

| | | | |
|---|---|---|---|
| 2006/0118472 A1* | 6/2006 | Schick et al. | 210/198.2 |
| 2007/0008060 A1* | 1/2007 | Weller et al. | 336/229 |
| 2008/0258735 A1* | 10/2008 | Quackenbush et al. | 324/445 |
| 2009/0267617 A1* | 10/2009 | Seyfi et al. | 324/655 |
| 2013/0335064 A1* | 12/2013 | Suzuki et al. | 324/201 |

* cited by examiner

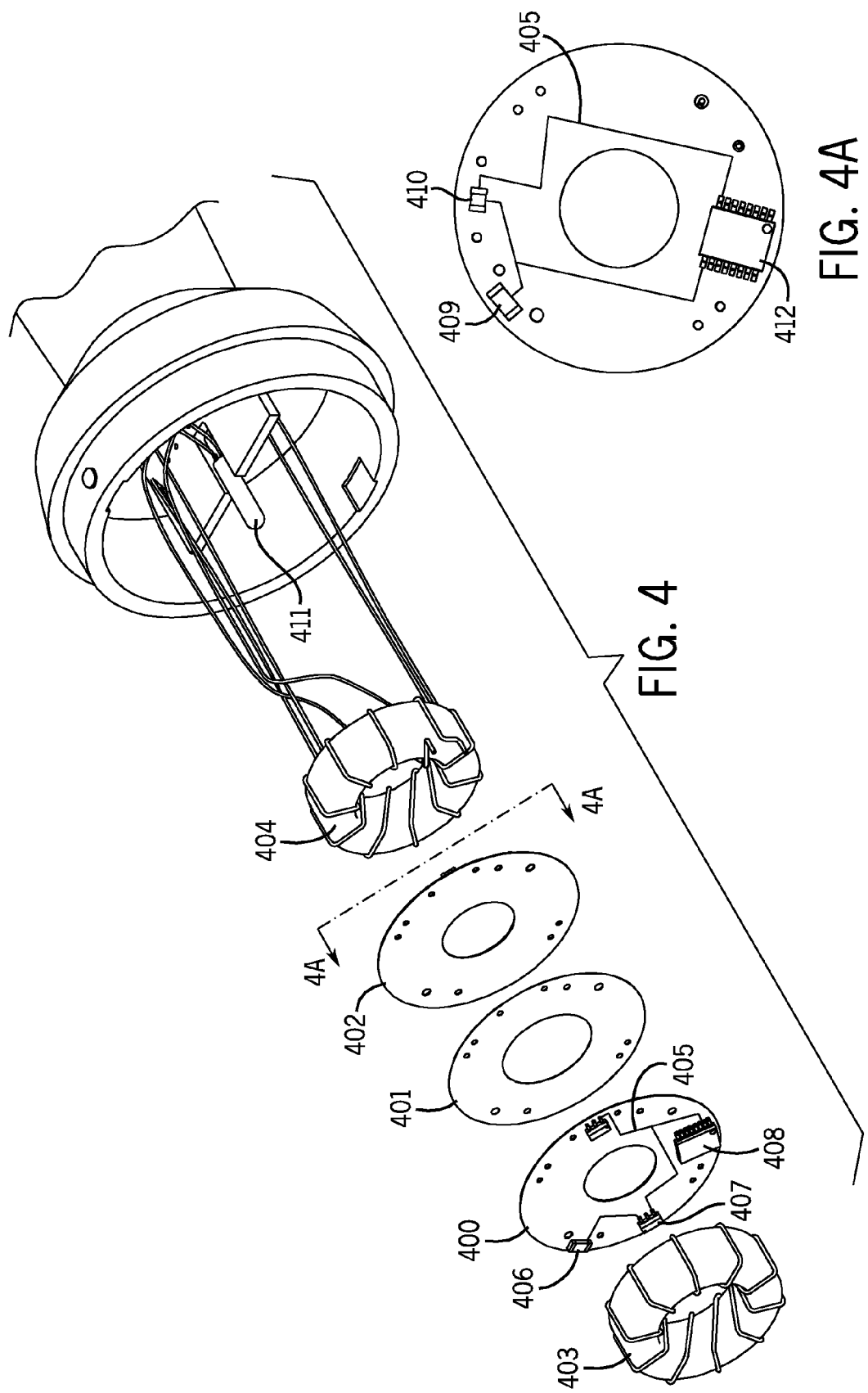

TOROIDAL CONDUCTIVITY PROBE WITH INTEGRATED CIRCUITRY

CROSS REFERENCE TO RELATED APPLICATIONS

This application is a U.S. National Stage Utility application taking priority from PCT application PCT/US2010/025651 filed Feb. 26, 2010, herein incorporated by reference, which PCT application takes priority from U.S. Provisional application No. 61/302,122 filed Feb. 6, 2010, and also herein incorporated by reference.

BACKGROUND OF INVENTION

References
  U.S. Pat. No. 2,542,057, M. J. Relis, Method and Apparatus for Measuring the Conductivity of an Electrolyte
  U.S. Pat. No. 3,806,798 Gross, Electrodeless Conductivity Measurement System
  U.S. Pat. No. 7,126,343 Howes, Conductivity Probe with Keeper
  U.S. Pat. No. 5,157,332, P. C. Reese, Three-Toroid Electrodeless Conductivity Cell
  U.S. application Ser. No. 12/410,443 Samad Seyfi, Apparatus and Method for Measuring Salinity of a Fluid by Inductance
  A. Lopes Ribeiro, "Inductive Conductivity Cell for Water Salinity Monitoring", XVIII Imeko World Congress, Metrology for a Sustainable Development
  U.S. Publication 2006/0118472 Karl G. Schick et. al., Single-Use Manifold and Sensors for Automated, Aseptic Transfer of Solutions in Bioprocessing Applications
  U.S. Publication 2009/0008060 A1 Samad Seyfi, Apparatus and Method for Measuring Salinity of a Fluid by Inductance
  U.S. Publication 2007/0008060 A1 Thomas M. Weller, Total Fluid Conductivity Sensor System and Method
  U.S. Pat. No. 2,774,239 E. R. Fitzgerald, 1956, Apparatus for Determining Dynamic Mechanical Properties of Viscoelastic Materials
  U.S. Pat. No. 6,586,939 Otto N. Fanini, 2003, Method and Apparatus for Reducing the Effects of Parasitic and Galvanic Currents in a Resistivity Measuring Tool
  U.S. Publication 2008/0258935 John K. Quackenbush, Non-Metallic Flow-Through Electrodeless Conductivity Sensor and Leak Detector
  U.S. Pat. No. 7,581,434 Frederick M. Discenzo 2009, Intelligent Fluid Sensor for Machinery Diagnostics, Prognosis and Control
  U.S. Pat. No. 7,285,420 Fredrick M. Discenzo, 2007, Fluid Sensor Fixture for Dynamic Fluid Testing
  U.S. Pat. No. 3,404,335 R. J. Kidder, 1968, Apparatus for Measuring Electrical Conductivity of a Conducting Medium Capable of Flowing in a Conduit
  U.S. Pat. No. 7,126,343 Ronald Bruce Howes et. al., 2006, Conductivity Probe with Toroid Keeper Conductivity of a fluid provides important information about its contents. For example, conductivity of water provides an indication of ionizable constituents of the water, such as salts. This has applications in process control, environmental remediation, and monitoring of water handling systems such as for salt and fresh water. The invention described herein relates generally to an instrument used for measuring the electrical conductivity of fluids. In this type of instrument, a magnetic inductor generates a magnetic field around a core, which may include a ferromagnetic material. This inductor-core combination is typically a electromagnetic coil or winding of toroidal shape, having an inner and outer circumference, as is well known to those in the art. The fluid for which one desires to measure conductivity is permitted into the volume inside the inside circumference of the toroids. A second toroidal coil senses the magnetic field generated by the first toroidal coil by means of magnetic coupling based on the electrical conductivity of the fluid and generates an electrical output related to the electrical conductivity of the fluid.

Electrodes have been used to directly measure conductivity in a liquid by applying a DC or AC voltage between a pair of electrodes and measuring current flow in the path. This has several disadvantages, such as electrolysis and corrosion changing the contact resistance of the electrodes, causing substantial calibration drift, and different behavior of loss mechanisms with frequency of excitation in the case of an AC signal. It can also be challenging for extreme situations like highly corrosive or ultrahigh purity fluids.

For this reason, electrodeless systems for conductivity measurement are commonly used such as that described in U.S. Pat. No. 2,542,057, issued on Feb. 20, 1951 to M. J. Relis for Method and Apparatus for Measuring the Conductivity of an Electrolyte. In that system and others which follow two toroids with multiple windings on each are arranged with some separation such that they align axially. An excitation alternating current voltage is applied to one coil, the drive, primary or excitation coil, which induces a magnetic field inside the toroid. The magnetic field then imposes a current in the fluid such that the electrical current flow path goes through the dual toroid assembly out and around the exterior and back into the center of the coils. The second toroid, referred to as the secondary or sense toroid is used as a sensing circuit. The current through the fluid produces a magnetic field in the sensing toroid. This magnetic field induces a current in the windings of the sensing toroid. The magnitude of the voltage across the sensing toroid is a function of the primary's voltage, water conductivity, and windings on both the primary and secondary.

Improvements such as the use of ferromagnetic cores and opposing windings, described in U.S. Pat. No. 3,806,798, issued on Apr. 23, 1974 to T. A. O. Gross for Electrodeless Conductivity Measuring System have been made since then. The two toroids are also typically encapsulated such that the region in the center and, in some cases such as in a bath or tank, the region outside of the toroids are exposed to the fluid under test but the fluid is prevented from going in between the two toroids or into the windings of the toroids.

As described in U.S. Pat. No. 5,157,332, issued on Oct. 20, 1992 to P. C. Reese for Three-Toroid Electrodeless Conductivity Cell, one can also use two outer drive coils and one inner sense coil located between the drive coils, which helps confirm by switching between drive coils that no fluid has penetrated the toroid cavity or windings. This patent also briefly describes a way of dealing with another, more subtle problem. The literature on double toroid devices of this type states that the toroid is very efficient and has self contained flux lines, so toroids can be mounted in very close proximity and have no cross talk. This turns out not to be completely true. The windings of the toroids capacitively couple from the primary toroid to the sensing toroid and impose a voltage on the sensing toroid. This results in inaccurate readings or even the complete inability to measure meaningful signals for low conductivity fluids. While this patent states that the primary shielding of the signal receiving coil is provided by the surrounding drive coils, metallic shields are also used to reduce the unwanted direct toroid-to-toroid coupling. These shields are described as "magnetic", however, so would not necessarily act to eliminate the capacitive coupling between drive and sense coils. In addition, in theory, a single ground plane with a shared ground between the two toroids such as described in that patent provides perfect shielding, but in reality, the ground has some impedance and therefore couples some of the high drive current from the primary side to the secondary side. This causes additional electrical noise in the sense coil and thus in the output of the conductivity sensor if multiple shields are all joined to a common ground, as in the Reese patent. Similarly, in U.S. Pat. No. 6,586,939 Fanini, issued in 2003 for "Method and Apparatus for Reducing the Effects of Parasitic and Galvanic Currents in a Resistivity Measuring Tool", although multiple grounds and shields are discussed they are in the context of preventing electrical cross-talk between the drive and sense toroids which is carried through the outer conductive casing of their conductivity measurement system. No mention is made of shielding between the toroids in order to reduce electrical parasitics due to coupling between the toroids, as occurs with a nonconductive casing.

In U.S. Publication 2007/0008060 A1 by Weller, "Total Fluid Conductivity Sensor System and Method", a PCB is used for the conductivity sensor, but as the coils are formed out of vias and microstrips on and within the PCB rather than with wires and ferromagnetic cores the PCB is acting as a structural material, and no conductive planes are used as shields between coils to reduce cross-talk. Their device is also not well suited to measurement of a broad range of solutions and conductivities, as it relies on a specific resonance.

By their nature, these conductivity measurement systems operate in an environment in close proximity to fluids which may be of different temperatures. Many parts in the systems may change their operating parameters as a result of changes in temperature. U.S. Publication 2006/0118472 Schick et. al., among others, discusses use of a temperature sensor exposed to the fluid being measured in order to perform temperature compensation of the apparatus. Increased circuit stability and performance can be obtained, however, by also measuring temperatures of components within the system directly. In particular, measurement of the temperature of the toroids as well as fluid temperature can improve circuit stability and performance.

Calibration of such an apparatus is necessary, both to establish initial performance of a particular device after construction and later in the field as components and environmental conditions change. U.S. Publication 2008/0258935 Quackenbush for "Non-Metallic Flow-Through Electrodeless Conductivity Sensor and Leak Detector" discloses using a conductive loop through the toroid openings with a single resistor for calibration of the system. Such a calibration system, however, presumes that any calibration curve will be a straight line through the origin. In the majority of real world measurement situations, a minimum of both a slope and intercept are needed to describe data, which requires 2 point measurement and 2 resistors of different values to be used for calibration. In many cases a curve defined by 3 or more points and 3 or more resistors may be necessary to fully describe a calibration data set.

Amplification of signals from the sense coil is also necessary for these systems. In U.S. Publication 2009/0008060 A1 by Samad Seyfi, a system for using resonance of the inductance of a gap in a toroid is described. While this method provides very high sensitivity, it applies only to a very narrow salinity range because it is tuned for a specific resonance, so does not solve the problem of measurements over a wider range of salinities. The ideal way to carry out amplification is to perform this operation as close as possible to where the signals are detected, i.e. the sense toroid, rather than by using wires carrying these low level signals long distances. This requires use of circuitry components near said toroid. While U.S. Publication 2006/0118472 Karl G. Schick et. al. discusses use of a PCB board in such a conductivity measuring system, the components described are merely present for measurements and data storage, and all data processing takes place outside in a user interface or controller system. There is no indication of signal processing, calculations, calibrations etc. taking place in the sensor area, where signals are strongest.

One way of boosting effective signal strength is by performing a differential signal comparison between the signal and sense toroids. U.S. Publication 2007/0008060 A1 by Weller, for "Total Fluid Conductivity Sensor System and Method" describes making such a comparison by extracting and comparing the imaginary components of the signals from the phase information in the signal. Such a method, however, loses the real part of the signal, which provides the conductivity. Comparing the real part of the signal would allow determination of conductivity from the amplitudes of the signals, which allows for operation at lower frequencies.

Thus, previous work in this field fails to address several issues with these types of conductivity probes. First, capacitive coupling between the toroids is not completely compensated, particularly for low conductivity fluids. The drive coil has a high level AC signal which may vary in frequency, amplitude, waveform, or duty cycle, causing corresponding variation in the magnetic field generated by this toroid. The sense coil reacts to the magnetic field as coupled by a conductive fluid, but electrostatic coupling also takes place between the drive and sense toroid, causing unwanted spurious signal from which the desired signal due to magnetic coupling must be extracted. Second, the signal coming from one or more sensing coils used in the probe is a "low level signal", in the millivolt range, making it easily susceptible to interference as it travels from the region of the toroidal sensor(s) to electronics which can be used to amplify it for readout by equipment or an operator. Third, depending on the method by which the toroids are sealed from fluid entry, when pressure on the sensor changes (as may happen if it is immersed in fluid), positioning of the toroids can change, causing changes in its response. Finally, assembly of these structures does not take full advantage of recent availability of integrated electronics and sensors which can improve ease of manufacturing and reduce costs to make such a conductivity sensor.

SUMMARY DISCLOSURE OF INVENTION

The present invention solves these and other problems as described below. One embodiment of this invention uses Printed Circuit Boards, or PCBs, for shielding to reduce capacitive coupling between drive and sense toroids mentioned previously. These PCBs can easily be obtained with one, two, or many layers of metal for shielding, and one or more of these layers can be grounded or floating as desired to provide shielding of the drive or sensing toroids. To make the assembly as compact as possible, a printed circuit board (PCB) with one or more metallic layers is placed in between the two toroids and is designed such that the metal layer on one side of the PCB provides a ground shield for the primary or drive toroid, while the metal layer on the other side of the PCB, if any, is independently grounded and provides the shielding for the secondary or sensing toroid. Intermediate isolated ground planes between the grounded out layers can provide further decoupling.

In another embodiment of this invention, circuitry, including active processing circuitry such as integrated circuits, can be mounted "situ" on PCB boards near the toroids, or mounted or inserted in some other region near the toroids. This allows conversion of low level millivolt signals from the sense coil of the conductivity probe to high level voltage or current signals, which can more easily be sent to distant control equipment or an operator without interference or degradation. Alternatively low level signals could be processed directly to digital signals in order to communicate with a computer control or analysis system. One example of this type of active processing circuitry is an Analog Front End (AFE) which could process and amplify signals locally, while another is an Analog to Digital Converter (ADC) which could convert DC signals to digital signals.

In another embodiment of this invention, circuitry mounted on PCB boards or mounted or inserted in some other region near the toroids can be used to send signals by methods including, but not limited to, infrared, optical or wireless transmission out to distant control equipment or an operator. This completely avoids use of signal wires leading away from the sensing area. Conversely, an external device could by methods including, but not limited to, wires, infrared, optical or wireless transmission send calibration data to local receiving circuitry for storage in circuitry containing internal memory elements which may include, but are not limited to, volatile or non-volatile memory. Antennas for transmission or reception of these wireless signals may be built into the PCB board or may be built into the circuit elements mounted on the PCB boards or inserted in some nearby region.

In another embodiment of this invention, temperature sensors can be mounted on PCB boards or mounted or inserted in some other region near the toroids in order to allow for temperature compensation of conductivity measurement. These sensors could be embedded directly on the integrated circuits used for signal processing, or could be standalone but with connections to processing circuitry such that low level signals can be converted to high level signals as described above. It is obviously possible to combine other types of sensors with the conductivity probe in the same way, such as a magnetic field sensor for probe calibration, leak detection sensors to ensure that fluid has not reached the toroids, vibration sensors and so on. Recent advances in Microelectromechanical systems (MEMS) allow for a wide variety of sensors in direct proximity to the conductivity probe system, given the nearby conversion to high level signals available.

In another embodiment of this invention, the ground plane closest to the sense toroid is connected to the Analog Front End (AFE) virtual ground. This is done because the sense toroid secondary is wired between the virtual ground and the AFE by means including, but not limited to, capacitive coupling. If capacitive coupling is used it provides further signal isolation.

In another embodiment of this invention, in order to get high signal strength and correspondingly high sensitivity, tank circuits are employed to have the toroids operating at or near resonance in an LC circuit using the toroid as the inductor and a capacitor of suitable value connected in parallel as the tank capacitor. This capacitor is preferably close to the inductor for temperature compensation. This method provides the maximum sensitivity to the signal of interest and has been used for many years in radio circuits. However, a problem arises from minor temperature deviations. Components including, but not limited to, the toroid(s) and tank capacitor change their resistances, inductances and capacitances with temperature causing a shift of the resonance frequency, resulting in a change in the signal amplitude which does not correspond to a valid measurement of fluid conductivity. Consequently, one or more temperature sensors are added to monitor the temperature of the toroids and their outputs are used as an input to the signal conversion algorithm in order to compensate for the changes in these components.

In another embodiment of this invention, differential or ratiometric signal comparison is used for greater inherent circuit stability with changes in temperature or other environmental factors. Comparison of outputs from AFEs from each toroid is made, so that changes in toroid properties due to environmental factors is factored out and less drift is seen in the resonance frequencies described above.

In another embodiment of this invention, self calibration is carried out in order to avoid individually calibrating each unit. By realizing sense signal response is proportional to the conductivity of the fluid, it is possible to build an internal coupling circuit that is switched on for calibration. In one implementation, one or more resistive wire loops are passed through and around the toroid assemblies and back to a control circuit. This wire loop could be arranged inside of the toroid assembly (but outside of the toroids) or used externally for one time calibration. When the device is known to be in atmosphere, the circuit(s) can be activated and the corresponding signals recorded from each resistive wire loop. In order to perform calibration when a fluid is present, the wire loop resistor having a known resistance value is placed effectively in parallel with the unknown resistance of the conductive fluid, forming an equivalent resistor. Additional resistors can be placed in parallel with the conductive fluid in the same way to form other equivalent resistors and provide additional information on the unknown resistance of the fluid. By knowing the relationship between the response and water conductivity and solving simultaneous equations, calibration factors can then be adjusted. Such measurements of equivalent resistance may be carried out by, but are not limited to, the circuitry on the PCB in order to provide "in situ" calibration, potentially even while the unit was in use. In particular the Analog to Digital Converter may be used for such measurements. It would be obvious to one skilled in the art that other forms of resistors, such but not limited to surface or wire mount resistors on or near the PCB, could also be used for this embodiment. It would also be obvious to one skilled in the art that external resistors and measurement devices could be used to calibrate the unit in this same way before it is placed in use.

In another embodiment of this invention, sensors may be used to compensate or calibrate the conductivity sensor for strain due to pressure changes, such as may be found from immersion in fluid. More specifically, depending on the sealing system used to prevent fluid penetration into the toroid and electronics, the complete package may not be rigid enough to prevent some changing of toroid positions relative to each other when pressure is applied, which changes their signal output. One way to compensate for this shifting is one or more strain sensors embedded in the structure. Signals from these strain sensors can be used to compensate conductivity sensor output for positional changes. Another type of sensor which could be used is a magnetic field sensor, which could directly read strength of the drive or primary toroid magnetic field and compensate signals coming from the sense or secondary toroid accordingly.

In another embodiment of this invention, different winding counts, winding spacings, ferrite cores materials, toroid cross sectional sizes, or central opening sizes may be used for each of the drive and sense toroids in order to individually optimize properties of each toroid. In one exemplary implementation, relatively wide spacings between windings in the drive toroid may be used for magnetic field generation, since this allows for higher frequency operation, lower L values, and a cheaper component, while relatively tighter spacings between windings and consequently higher winding count may be used in the sense toroid for higher sensitivity.

BRIEF DESCRIPTION OF DRAWINGS

FIG. 2a. shows an expanded view of an electrical shield with separate grounds for the two PCB metal layers.

FIG. 4. shows the construction of a conductivity probe in accordance with the invention described herein, with two PCB ground planes and integrated circuitry such as, but not limited to, an Analog Front End (AFE) and an Analog to Digital Converter (ADC).

FIG. 4a. shows the back side of one of the PCB boards from FIG. 4a. with integrated circuitry including an exemplary environmental sensor.

MODE(S) FOR CARRYING OUT THE INVENTION—DETAILED DESCRIPTION

The present invention and its various embodiments are described below, with reference to figures as necessary. Reference numbers are used to match particular elements described in the text with those shown in figures.

Figure 1:
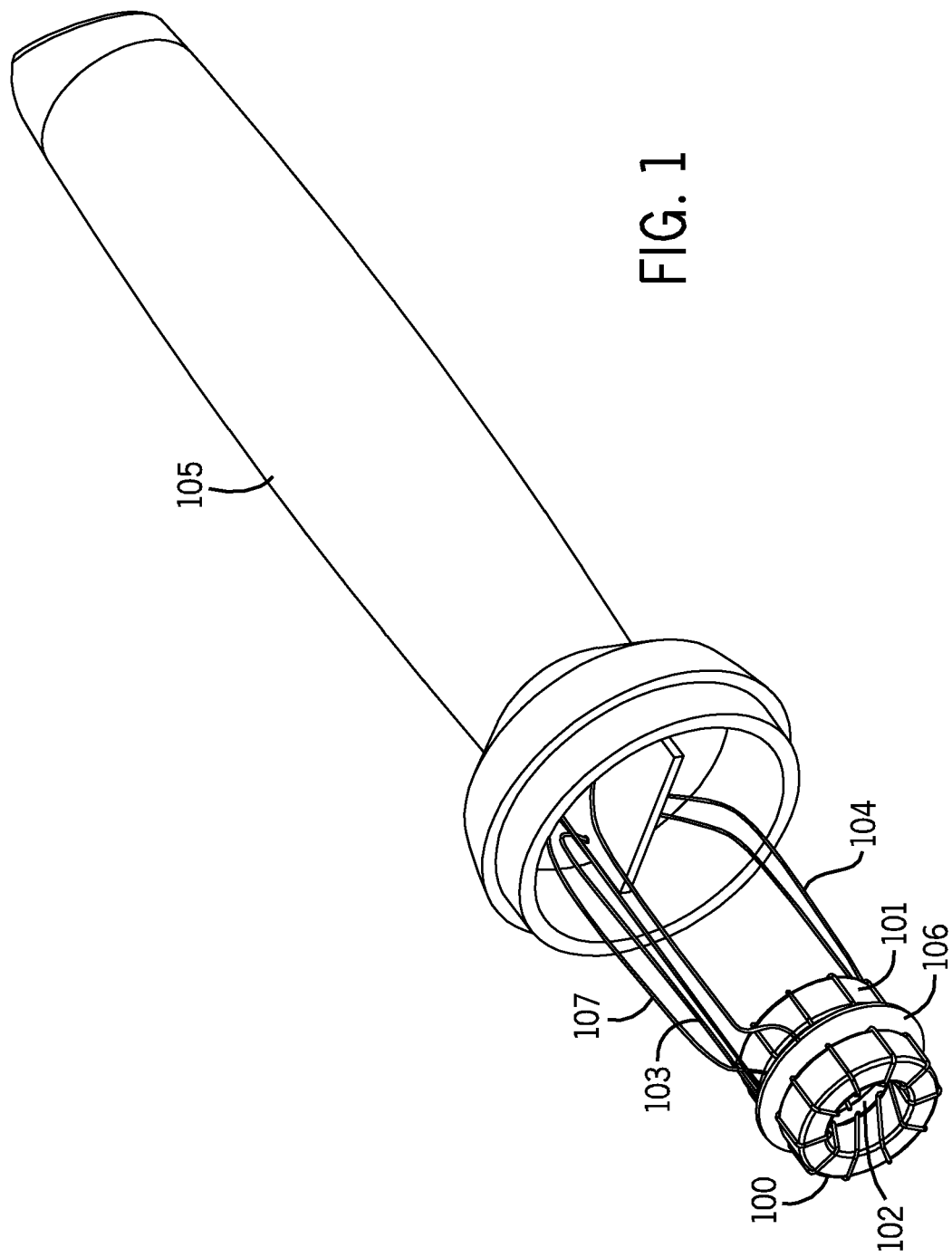
FIG. 1 illustrates the design of a typical magnetic toroid based conductivity probe as previously constructed.

Generally speaking, the present invention describes an apparatus and associated methods of construction and operation for carrying out conductivity measurements of a fluid. FIG. 1 illustrates a conventional conductivity probe, as previously constructed. The apparatus includes at least two magnetic inductors 100 and 101, often referred to as toroids in this description though it should be appreciated that they can take other shapes, and associated magnetic circuits. These toroids are coaxially stacked around a central aperture 102 which permits fluid to flow through the aperture. This central aperture is commonly, but not exclusively, circular. AC power is supplied by means of power wires 103 to the drive or primary toroid 100 in order to generate a magnetic field. Low level, millivolt signals are generated by magnetic coupling of the AC fields from the drive toroid 100 to the sense toroid 101 through a conductive liquid in this central aperture. These signals can be related to the conductivity of the liquid according to principles well known in the art. Signal wires 104 extend from the sense toroid 101 through a handle 105 to a set of electronics (not shown) which convert the low level signals to higher level voltage or current signals and which ultimately provide information on conductivity of the liquid to a readout system or operator. In some cases shielding 106 is provided between the two toroids 100 and 101, which may be grounded by wires 107. A housing which is not shown is typically used to protect the toroids and wires from the conductive fluid and environment, this may take many forms depending on the particular application for which the conductivity sensor is used.

An important feature of the invention described herein is use of Printed Circuit Boards, commonly abbreviated as PCBs, for several purposes. A variety of materials and manufacturing methods are used to produce these PCBs, for example FR-4 (woven glass and epoxy) is the most common material but FR-2 (phenolic cotton paper) may be used for cost sensitive applications where thermal expansion and vibrational considerations are minor. A wide variety of manufacturers can easily produce PCBs with any desired geometry, metal coating on one or both sides, and circuit trace layouts for addition of passive (e.g. capacitors, resistors, inductors) and/or active (integrated circuits) devices. More recent investigations into integrating circuitry directly into PCBs has led to the ability to embed multiple layers of metal by stacking thin PCBs or by forming them as the PCB is manufactured. Some types of passive devices like, but not limited to, resistors and capacitors can also be fabricated in that way. It can be appreciated by one skilled in the art that other insulating materials not commonly associated with PCBs could be substituted for conventional PCB materials, including but not limited to wood, paper, plastic, glass, ceramic or elastomers. Any insulating material available in sheet form and which can be coated with a conducting layer can be used for the purpose of this invention. Use of the term "PCB" or "PCB board" in the description of this invention is hereby considered to include these alternatives. Similarly, though the term "metal" is frequently used to refer to the conductive material used for ground planes and wiring interconnects in this invention, it may be appreciated that any conductive material, such as but not limited to conductive oxides or conductive plastics, could be substituted for the metal.

The first purpose of using these PCB board based ground planes in the invention described herein is to provide electrical shielding between the toroids. As previously mentioned, windings of the toroids capacitively couple from the primary toroid to the sensing toroid and impose a voltage on the sensing toroid. This results in inaccurate readings or even the complete inability to measure meaningful signals for low conductivity fluids. In theory, a single ground plane with a shared ground between the two toroids provides perfect shielding, but in reality, the ground has some impedance and therefore couples some of the high drive current from the primary side to the secondary side. Having two independent grounds and shields further improves the decoupling between the two toroids, allowing greater sensitivity of the conductivity probe. Having still more ground planes, some grounded and some floating, could still further improve decoupling, at some cost in additional fabrication complexity. Using PCBs for these additional conductive layers, though, is advantageous in that these additional conductive layers can be added and electrically connected as desired at minimal cost.

The PCB board can be readily shaped by processes well known in the art into a shape suitable for incorporation into the double toroid conductivity probe system. In particular, it would have a central aperture coaxially located with the apertures of the toroids, and have an outer extension to or past the outer boundaries of the toroids suitable for providing electrical shielding. It can be appreciated that the central aperture in such a PCB structure can be formed in a variety of shapes other than circular as needed for fluid passage in a sensing or control system.

Figure 2:
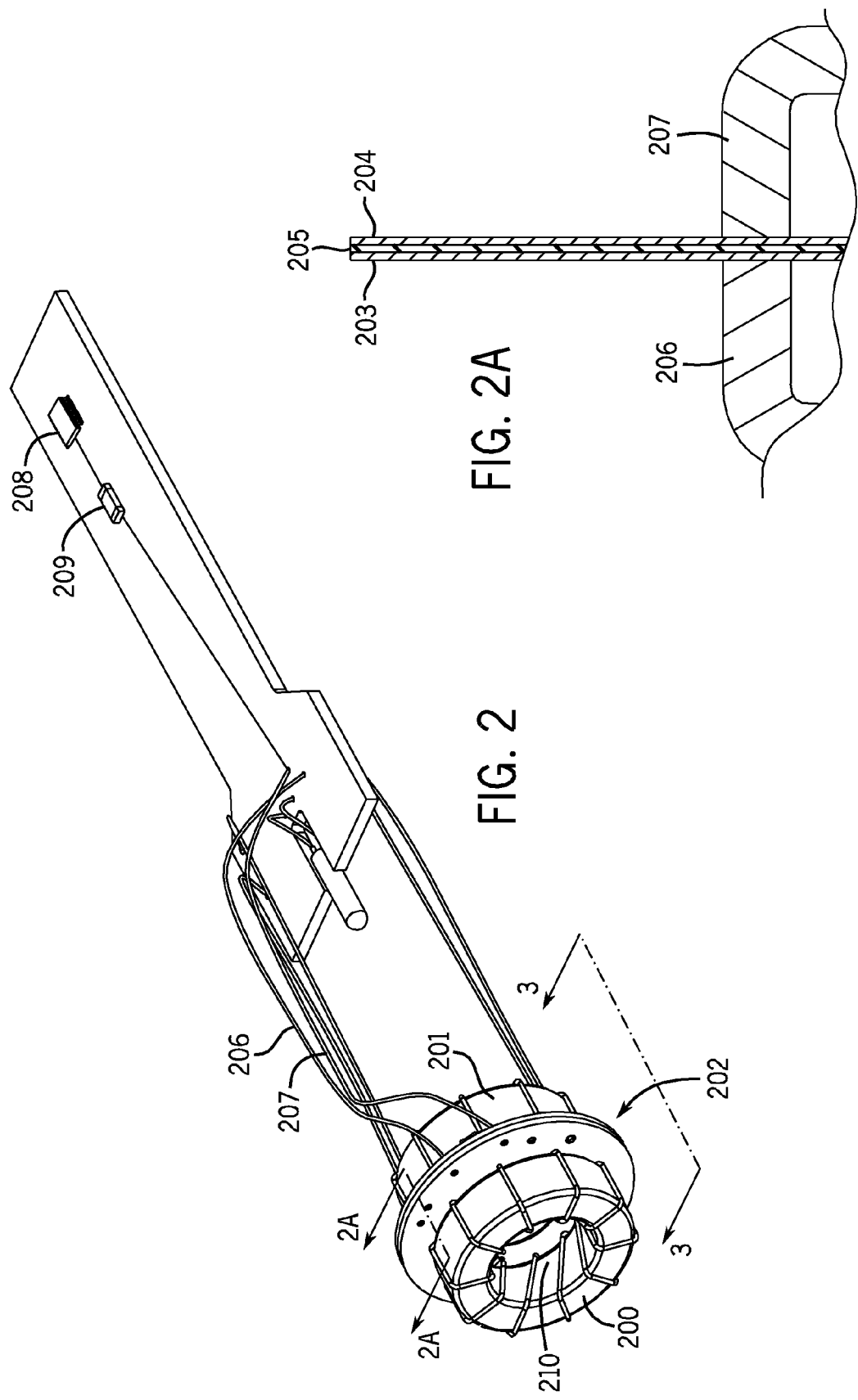
FIG. 2. shows the construction of a conductivity probe in accordance with the invention described herein, with two PCB ground planes.

FIG. 2 shows a conductivity probe constructed in accordance with this invention. In addition to the signal toroid 200 and sense toroid 201 there is a double layered electrical shield 202. As seen in magnification in FIG. 2a, this shield has two grounded sides 203 and 204, arranged around an insulating layer 205 making use of the PCB board 202 and its associated top and bottom metal layers. One side of the signal toroid 200 is connected to the system ground, and the other side is connected to the AC drive or excitation signal. Ground plane 203, the shield facing the signal or drive toroid, is connected to the system or power ground by means of wire 206. Ground plane 204, closest to the secondary or sense toroid 201, is preferably connected by means of a wire 207 to the virtual ground of an Analog Front End (AFE) 208 which may be placed in a location such as in the handle of the unit. This may be done if the sense or secondary toroid is wired between the virtual ground and the AFE by means of capacitive coupling using a coupling capacitor 209. The use of the virtual ground on the sense AFE provides further noise isolation as it is less affected by ground noise caused by nearby high currents on the primary. The PCB board shield is lined up coaxially with the two toroids with its aperture 210 lined up with the apertures of the two toroids 200 and 201. It may be appreciated that methods other than wire bonding, including but not limited to strap bonding, solder bump bonding and ball grid array (BGA) bonding may be used to connect metal layers 203 and 204 to grounds.

It may also be appreciated that use of these PCB board shields could be extended to conductivity probes using multiple toroids, placing shields between each set of signal and sense toroids to decouple them electrically and improve signal to noise ratio with shared or separate grounds. In a preferred implementation these toroids have inductances in the range of 200 microHenries to 400 microHenries, but other values may be used depending on the application. In a preferred implementation AC frequencies of 200 kHz with a 20% positive duty cycle may be used, while in another preferred implementation a 1 MHz sine wave may be used. Other input waveforms which may vary in frequency, amplitude, waveform type, or duty cycle may be used depending on the application.

It may also be appreciated that due to the electromagnetic symmetry of an arrangement of two toroids such as that shown, it would be possible to use toroid 201 as the signal toroid and toroid 200 as the sense toroid, arranging sides of shielding and grounds accordingly. Such an arrangement, with the sense toroid deeper in the fluid being measured, may have advantages for reduction of noise in certain environments. Thus all descriptions of this invention should be considered to apply to either physical arrangement of toroids, shields, and circuitry, as well as addition of further toroids and shields.

It is also apparent that different winding counts, winding spacings, ferrite cores materials, toroid cross sectional sizes, or central opening sizes may be used for each of the drive and sense toroids in order to individually optimize properties of each toroid. In one exemplary implementation, relatively wide spacings between windings in the drive toroid may be used for magnetic field generation, since this allows for higher frequency operation, lower inductance (L) values, and a cheaper component, while relatively tighter spacings between windings and consequently higher winding count may be used in the sense toroid for higher sensitivity. In another exemplary implementation, the inductance of one toroid can be shifted by use of a different inductor core material such as, but not limited to, "soft" steel, silicon steel, Carbonyl iron, and ferrites such as $ZnFe_2O_4$, an example of the spinel family. Among other things this would allow use of a different frequency, which could be more optimal for a particular conductivity sensor application.

Figure 3:
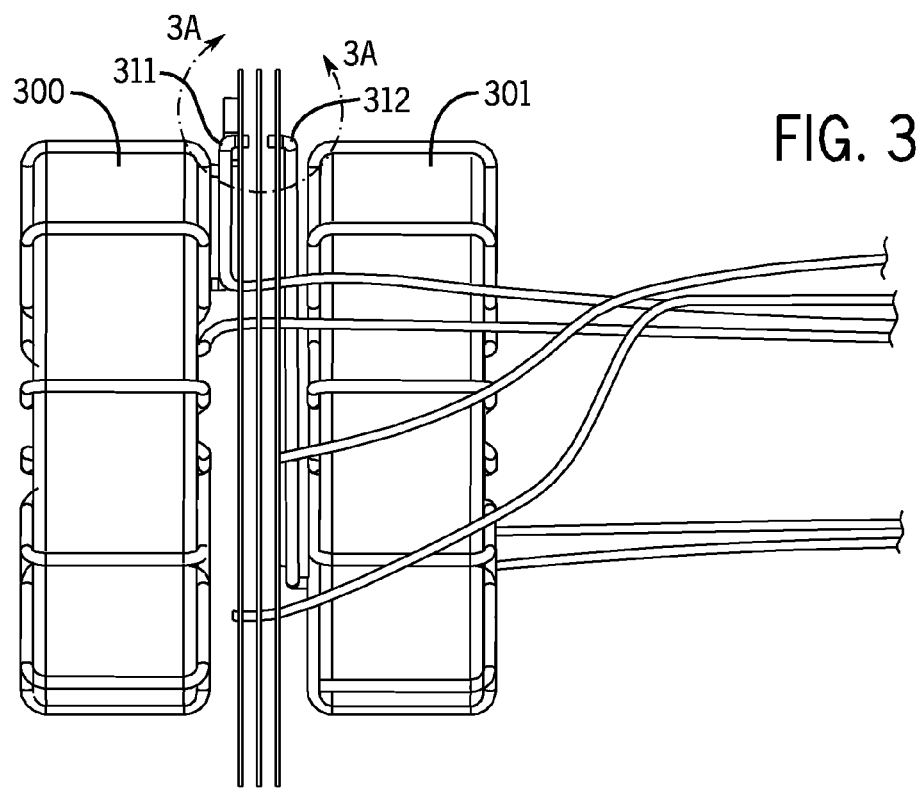
FIG. 3. shows the construction of a conductivity probe in accordance with the invention described herein, with a plurality of PCB ground planes.
Figure 3A:
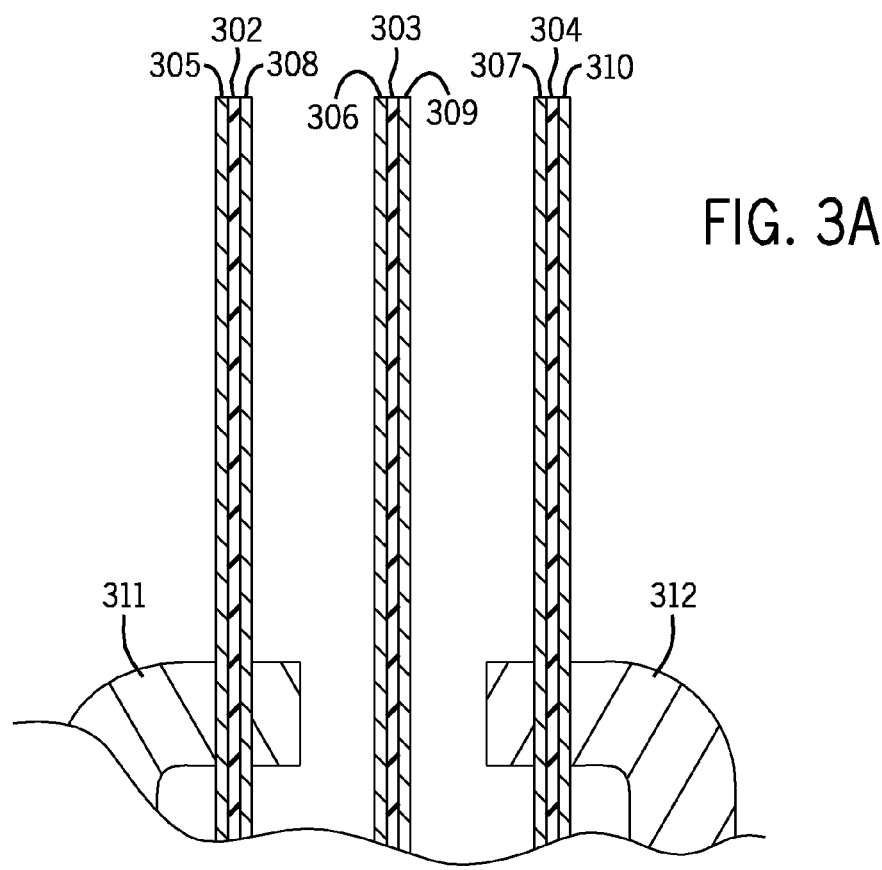
FIG. 3a. shows an expanded view of an electrical shield with multiple grounded and ungrounded layers.

As shown in FIG. 3, use of PCB board based shields allows for convenient addition of a plurality of ground planes between the signal toroid 300 and the sense toroid 301. This can be achieved either by using PCBs with additional embedded metal layers or by stacking conventional PCB boards 302, 303, 304 with metal layers 305, 306, 307 on the tops and other metal layers 308, 309, 310 on the bottoms. Said additional layers can be used for additional shielding and/or decoupling of the toroids, as well as, but not limited to, ground planes for circuitry. In one implementation ground planes 305 and 308 are connected to the power ground of signal toroid 300 by means of wire 311, while ground planes 307 and 310 are connected to the virtual ground used by sense toroid 301 by means of wire 312. These ground planes can also be ungrounded or floating as shown for metal layers 306 and 309, which may be useful for improved shielding. It is also apparent that multiple toroids could be stacked, some for magnetic field generation and some for sensing, each with PCB based electrical shields, potentially allowing for increased signal generation, a wide variety of optimal designs or calibrations of a single sensor head for fluids of various conductivities, and redundancy in case of fluid leakage or toroid failure.

By designing the PCB boards with necessary electrical connections by means including, but not limited to, metal filled or coated vias, connector straps and wire bonds, as well as with necessary cut-outs in the PCB boards assembly of the final stack can be done with relatively few connections needed to toroids or external wiring. It can be readily seen by one skilled in the art that any arbitrary combination of grounded and ungrounded layers separated by insulating layers can be designed into a single PCB board or set of PCB boards in order to achieve desired decoupling performance between a pair of toroids. In addition it is possible to use separate ground planes for circuitry and for each toroid, if this is desirable, by means of multiple metal layers in a single PCB board or by means of multiple PCB boards in the stack.

As shown in FIG. 4, in placing PCB boards 400, 401 and 402 between signal toroid 403 and sense toroid 404 one can make use of the intended function of a PCB board and place circuitry on said PCB boards. In particular, one can pattern metal traces 405 on these PCB boards in order to connect passive 406 and active 407, 408 circuitry needed to perform signal conditioning of low level (millivolt range) electrical signals generated by the sense toroid(s) and convert it to higher level voltage or current signals for a process controller or operator (not shown). Passive circuit elements 406 can include, but are not limited to, capacitors, resistors and inductors, which elements can take forms including, but not limited to, through-wire, surface mount or embedded devices. Active circuit elements can include, but are not limited to, transistors, diodes, and integrated circuits such as Analog Front Ends 407 and Analog to Digital Converters 408. Integrated circuits can be used for simple signal amplification, or with more customized designs, can be used for advanced functions such as compensation of temperature, range shifting, and generation and/or control of an oscillating signal for the signal toroid. It is also possible by use of different custom integrated circuits to convert these low level signals to other types of signals including, but not limited to, digital signals, infrared signals, optical signals or wireless signals, which could be passed out in that form to a process controller or operator. It is also possible to mount AFE 208 and capacitor 209 described in FIG. 2 on or near the PCB board between the toroids.

Such a use of the PCB board to support circuitry has several advantages. First, it improves signal to noise ratio as it is not necessary to transmit low level, e.g. millivolt or microamp range, signals long distances over lines subject to interference, particularly in electrically "noisy" environments such as one may find in process control equipment. Second, it reduces cost of a final system if a modular conductivity sensor can include its own sense and calibration circuitry as needed for its own particular configuration and this modular sensor can send information directly to a general purpose relay, programmable logic controller (PLC), computer or readout device. This becomes possible if the output of the modular sensor is in a standard format such as, but not limited to, 0-5 VDC or 4-20 mA analog signals, RS-232 or RS-485 digital signals, or Bluetooth (RF) or IrDA (infrared) wireless signals. This also allows circuitry on or near these PCBs to receive updated information via wire or wirelessly, such as but not limited to by means of RF, infrared or optical transmission, for purposes such as, but not limited to, calibration or range changes. This circuitry can also have elements for storage of said updated information including, but not limited to, volatile or nonvolatile memory which may be embedded in other circuit components or in the form of standalone memory components.

In an exemplary application of this conductivity sensor, a desired output signal is ppm salt. To achieve this accurately, three transfer functions are implemented. Stage 1 is conversion of the analog voltage signal from the signal toroid to conductance. Stage is 2 is a transformation from conductance to conductivity, generally a multiplication factor. Stage 3 is a transformation from conductivity to salt ppm. These transfer functions benefit from several types of temperature measurement. In particular, the toroid material has a permeability that is temperature dependant, and for which empirical measurements are needed in the transfer function of Stage 1 signal conversion. This function is different from that for the compensation of salt waters' conductivity change due to temperature, which also needs to be built from empirical data for the stage 3 transfer function. In an alternative embodiment, the stage 2 transfer function is not required to get the salt ppm, and can be avoided by using the temperature compensated conductance to feed directly into the temperature compensated ppm salt transformation.

The availability of passive and active components and circuitry in the immediate vicinity of the toroids in this invention allows for another embodiment, shown in FIG. 4a. A variety of circuit elements which take the form of miniature sensors widely known to those skilled in the art are now available in a chip or board mountable form, such as those used for CPU temperature sensing in computers. To take one exemplary type, a circuit element 409 which is a temperature sensor can be mounted on a PCB board or mounted or inserted in some other region near the toroids 403 and 404 in order to allow for temperature compensation of conductivity measurement, which may be very important depending on the control concept used for the probe as discussed previously. In one exemplary implementation circuit element 409 which is a temperature sensor may, instead of being placed on a PCB board, be placed in direct contact with one of toroids 403 and 404 in order to carry out temperature compensation of the toroids. These temperature sensors can be embedded directly on the integrated circuits used for signal processing, or can be placed elsewhere in the conductivity probe enclosure but with connections to nearby processing circuitry such that low level signals can be converted to high level signals as described above. In another exemplary type, circuit element 409 could take the form of a strain sensor to compensate output of the conductivity cell for pressure changes around the unit which could affect parameters including, but not limited to, inter-toroid spacing or values of other circuit components. In another exemplary type, circuit element 409 could take the form of a magnetic field sensor to compensate output of the conductivity cell for environmental changes around the unit which could affect parameters such as, but not limited to, signal toroid magnetic field output or coupling to the sense toroid. It is obviously possible to combine other types of sensors with the conductivity probe in the same way, including but not limited to magnetic field sensors for probe calibration, leak detection sensors to ensure that fluid has not reached the toroids or windings, vibration sensors and so on. Recent advances in Microelectromechanical systems (MEMS) allow for a wide variety of sensors in direct proximity to the conductivity probe system, given the nearby conversion to high level signals available.

One possible method of processing the signals involves placing the toroids in a "tank circuit", using capacitors in parallel with said toroids to achieve circuit operation at or near resonance for improved signal response. This has the advantage of substantially improved sensitivity for conductivity measurement, but the disadvantage of substantial temperature sensitivity so that measurement of temperature and active temperature compensation must take place in the sensor. Both the toroids 403 and 404 and the tank capacitors 406 and 410 shift with temperature causing a shift of the resonance frequency, resulting in a change in the signal amplitude. Consequently, at least one temperature sensor 411 is added to monitor the temperature of the fluid whose conductivity is being measured and is used as an input to the signal conversion algorithm. Preferably at least two temperature sensors are used, since when the conductivity sensor is first put in or near a new environment, such as but not limited to when the fluid whose conductivity is being measured flowing through or around the conductivity sensor changes temperatures, temperatures in different parts of the apparatus can change at different rates. In order to have stable operation as soon as possible, one embodiment of this invention may include a temperature sensor 411 in contact with or near the fluid in order to monitor its temperature, and a temperature sensor 409 on or near the tank capacitor(s) 406 and 410 in order to monitor their temperature. This also allows for the possibility of using nearby circuitry 412 to adjust voltages, frequencies, amplitudes or other circuit excitation parameters in real time to place or keep the circuit in resonance. While not required, it is clearly advantageous to have such compensation or control circuitry near the components being controlled.

Another extreme of signal processing involves putting no capacitors in parallel, which provides a very uniform response across a wide range of environmental conditions but lower sensitivity. Other circuit designs well known in the art between these two extremes may also be used, depending on the temperature range in which the probe may be used and the sensitivity versus the absolute measurement accuracy needed for a particular fluid conductivity application.

Figure 5:
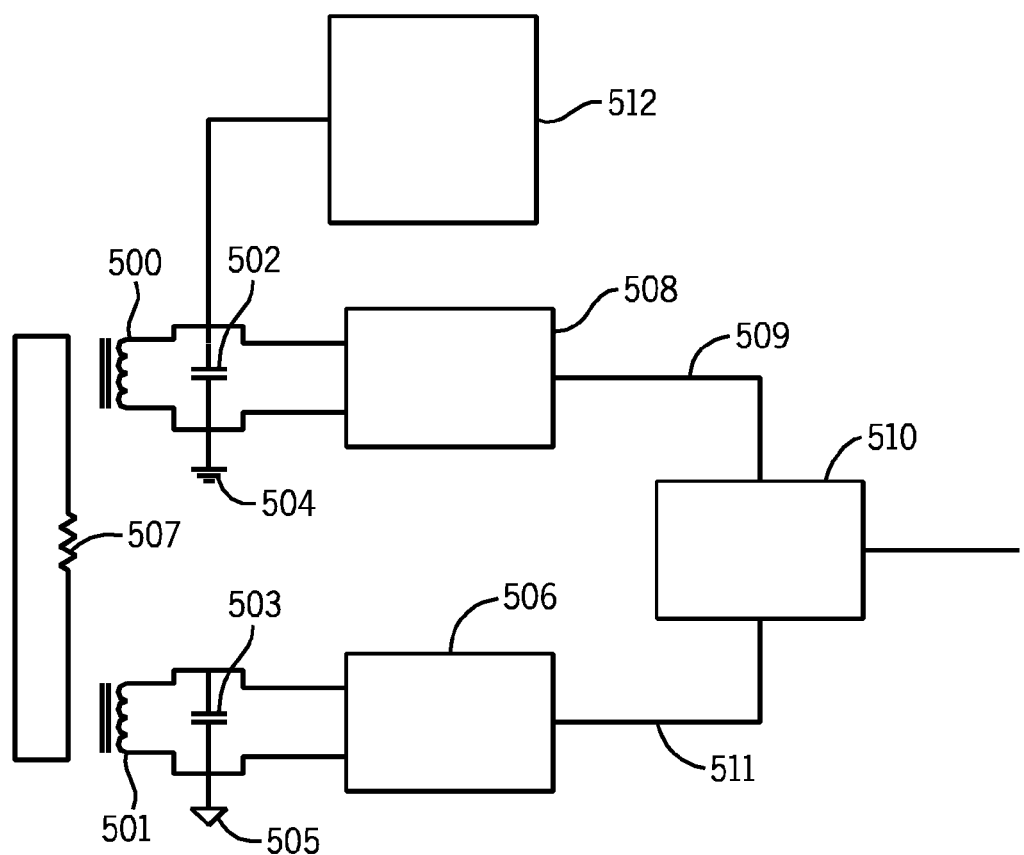
FIG. 5. shows a conductivity probe sensing electronics block diagram of a tank circuit including two Analog Front Ends and an Analog to Digital Converter.

FIG. 5. shows a block diagram for a circuit for a dual toroid conductivity measurement method using a LC tank circuit and two Analog Front End (AFE) integrated circuits in order to make a differential or ratiometric measurement. In a tank circuit, the signal toroid 500 and the sense toroid 501 are each placed in LC circuits in parallel with tank capacitors 502 and 503 respectively. The tank circuit for the signal toroid is preferably grounded to the power ground 504, and the tank circuit for the sense toroid is preferably grounded to the virtual ground 505 for an AFE. The sense toroid 501 provides an AC signal to AFE 506 based on fluid conductivity 507. The signal toroid 500 provides an AC signal to AFE 508 with a certain amplitude and phase. The output of each AFE is a clean DC signal representing a combination of amplitude and phase shift information about the signal from each toroid. The DC signal from AFE 508 for the signal toroid 500 is used to feed the reference 509 of an analog to digital converter (ADC) 510. The DC signal output from AFE 506 is sent to the signal input 511 of the Analog to Digital converter (ADC) 510. It is important that the signal conditioning gains from the AFEs be as close as possible for this to generate a useful differential signal. The resulting digital conversion from the ADC 510 is now a ratio of the signal 511 compared to the reference 509 and provides better signal integrity as the temperatures change or components drift, since a similar drift can be expected from each set of components. This is particularly important for a tank circuit, in which the LC resonance can provide a highly sensitive conductivity measurement but for which said resonance is also highly sensitive to values of components in the circuit including, but not limited to the toroids, capacitors, and power supply 512, which, in turn, are highly sensitive to temperature.

Figure 6:
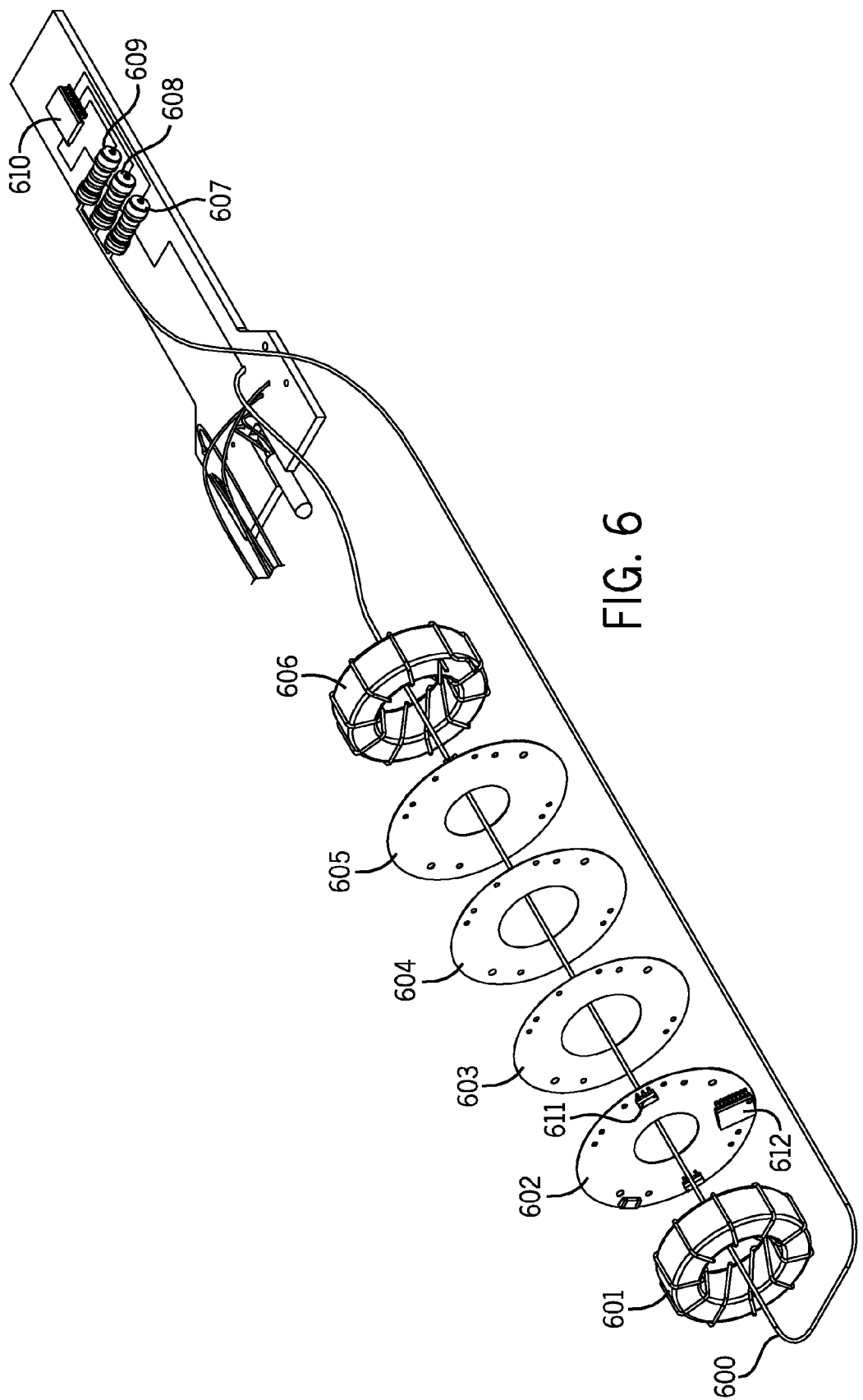
FIG. 6. shows where a resistive wire loop may be placed through the toroids in order to carry out self calibration of the unit using a wire loop and internal resistors.

FIG. 6. shows a calibration system to allow convenient calibration of each sensor unit, either before or during use. By realizing sense signal response is proportional to the conductivity of the fluid, it is possible to build an internal coupling circuit that is switched on for calibration. A wire 600 is passed through the apertures of signal toroid 601, PCB boards 602, 603, 604 and 605, and sense toroid 606, thus placing it in the volume where fluid conductivity would be measured. In one implementation of this invention, a single resistor 607 is placed in series with the wire 600 and while the sensor is in air, the known resistance of the material in the aperture can be used to calibrate the sensor circuitry before use. In this implementation, the wire and resistor assembly can, but does not need to be, a separate unit from the conductivity sensor and the wire 600 placed in the aperture only when calibration of the sensor is taking place. It is also possible to keep this wire and resistor assembly always in place, providing it is protected from the fluid, and activating it for calibration only when a fluid of known resistivity or of negligible resistivity, such as air, is in the aperture.

In another implementation of this invention this wire 600 is connected to two or more resistors 607, 608 and 609 of differing resistances. These resistors are placed individually by means of a switch 610 in series with the wire passing through the apertures. Although the switch shown is an integrated switch, it is apparent to one skilled in the art that other switches including, but not limited to, slide, toggle, reed, and rotary switches could be used for switching between resistors. In order to perform calibration when a fluid is present, the wire loop resistor having a known resistance value due to resistor 607 is placed effectively in parallel with the unknown resistance of the conductive fluid, forming an equivalent resistor. Additional resistors 608 and 609 can be placed in parallel with the conductive fluid in the same way to form other equivalent resistors and provide additional information on the unknown resistance of the fluid. By knowing the relationship between the response and water conductivity and solving simultaneous equations, calibration factors can then be adjusted. Such measurements of equivalent resistance may be carried out by, but are not limited to, the circuitry in IC 610 or other circuitry 611 on a PCB 602 in order to provide "in situ" calibration, potentially even while the unit was in use. In particular the Analog to Digital Converter 612, perhaps with custom application specific integrated circuitry and/or programming, may be used for such measurements and calculations. It would be obvious to one skilled in the art that other forms of resistors, such as but not limited to surface mount, wire mount or embedded resistors on or near any PCB, could also be used for this embodiment. It would also be obvious to one skilled in the art that external resistors and measurement devices could be used to calibrate the unit in this same way with a fluid representative of the fluid which it will be measuring conductivity of before the sensor is placed in use, or a reference fluid with known resistivity. If the wire is suitably protected it is possible to leave the wire in place in the fluid when the sensor is in use, and perform calibrations using the system described even when the sensor is in place or in use. It is also clearly possible to place these resistors and associated processing circuitry on one of the PCBs near the toroids such as 602 or 605.

Figure 7:
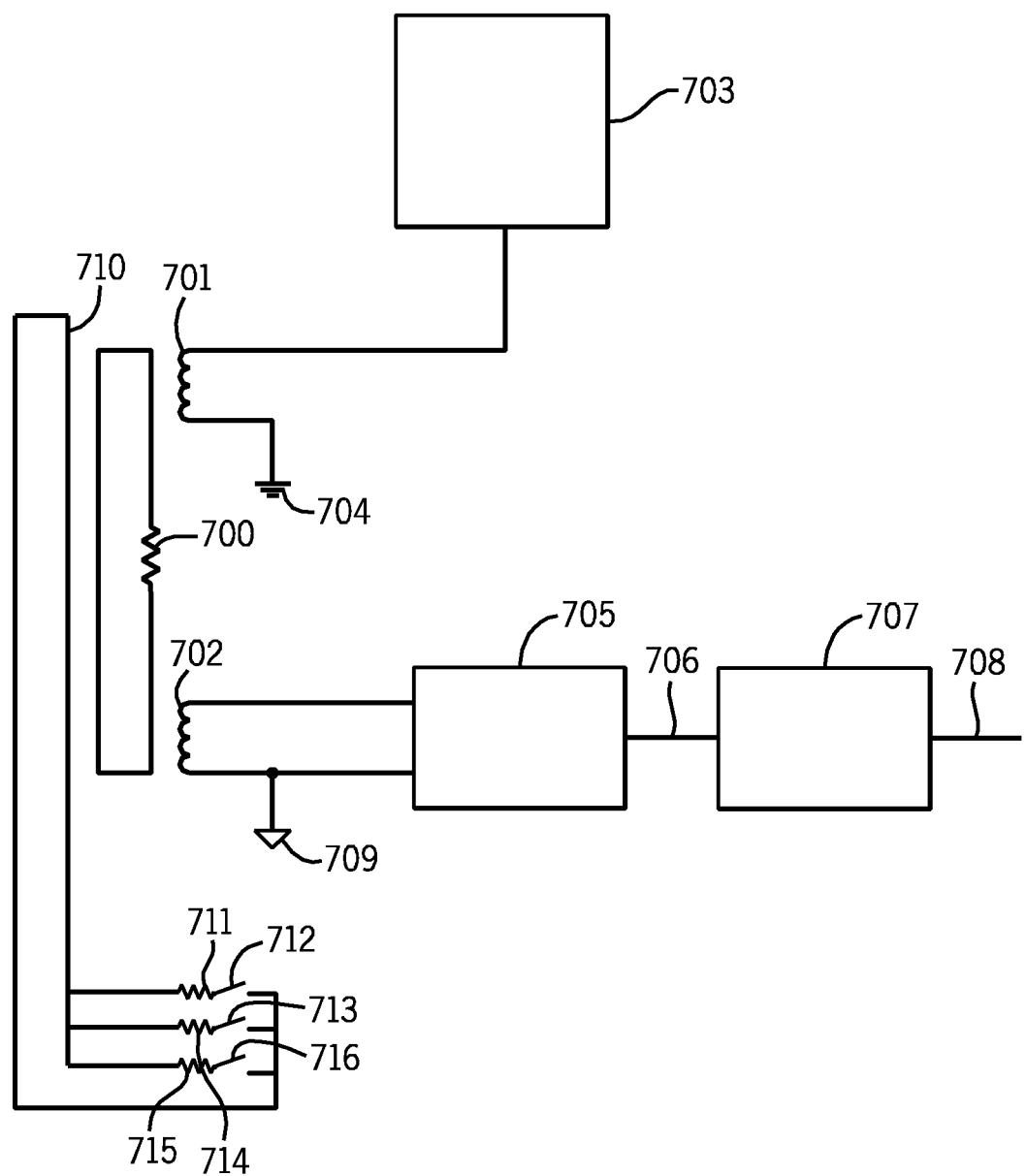
FIG. 7. shows a conductivity probe sensing electronics block diagram of a self calibration circuit including multiple resistors and an exemplary method of reading signals for calibration.

FIG. 7. shows a circuit block diagram for the calibration system described above. Unknown fluid resistivity 700 is measured using signal toroid 701 and sense toroid 702. Signal toroid 701 gets power from a power supply 703, and is grounded to the power ground 704. Sense toroid 702 sends a signal to an Analog Front End (AFE) 705, which provides a DC output 706 to ADC 707, which sends a measurement 708 out to the user. Sense toroid 702 and AFE 705 share a virtual ground 709. Wire 710, which was represented by 600 in FIG. 6, passes through the same or similar location as the fluid in the aperture of the toroids and shields. It is connected to at least one resistor 711 in an implementation where calibration takes place without the presence of a fluid of unknown conductivity 700. When a fluid of unknown conductivity 700 is present, the wire loop resistor assembly having a known resistance value due to resistor 711 is placed effectively in parallel with the unknown resistance 700 of the conductive fluid, forming an equivalent resistor. A switch 712 is used to disconnect resistor 711 and switch 713 is used to connect resistor 714 of different resistance value then resistor 711 into the circuit. These resistors 711 and 714 being alternately placed in parallel with the conductive fluid 700 form different equivalent resistors and provide information on the unknown resistance of the fluid 700. By knowing the relationship between the response and water conductivity and solving simultaneous equations, calibration factors can then be adjusted by other circuitry. For further precision of calculation or other ranges of fluid conductivities additional resistor 715 and switch 716 combinations can be used in as many additional pairs as may be desirable. Such measurements of equivalent resistance may be carried out by, but are not limited to, the circuitry in IC 705 or IC 707 or other circuitry in order to provide "in situ" calibration, potentially even while the unit was in use. It will be apparent to those skilled in the art that the resistors being switched into this circuit may be combined in any way, via series or parallel, providing enough information is available for solution of the equations. It will also be apparent that the resistors need not be switched with separate switches, and that they can be added together rather than alternately and individually placed into the circuit. It will also be apparent that multiple wire loops 710, each with a resistor, can be used for this calibration rather than using merely one wire and multiple resistors. This could be for reasons including, but not limited to, increased precision, reduced switch complexity, increased reliability, or improved redundancy.

Calibration data thus obtained can be sent by wire or wirelessly to an external unit for storage, or can be stored in local memory in circuitry on the PCB in the handle or in circuitry on or near the PCBs between the toroids. It could also be sent out for evaluation or processing and calibration or compensation parameters sent back to local circuitry for conductivity sensor operation. In this way operation of the sensor can be held within very narrow parameters, particularly if frequent or continuous in-situ calibration takes place by means of the resistivity system herein described.

A variety of methods known in the art are available for sealing the apparatus described above from the environment in which it operates and/or the fluid whose conductivity is to be measured. These include, but are not limited to, NEMA rated boxes, encapsulation in epoxy, resin, plastic, potting compound or elastomers by means of dipping or spraying, and casting the apparatus in a form filled with some insulating material which dries or sets to provide a desired final shape. In any case, it is important that the material in and between the toroids be "magnetically transparent", that is to say that it not interfere with the magnetic flux which must pass from the magnetic field generating toroid to the magnetic flux sensing toroid. Depending on the application of the conductivity probe, it may be useful or necessary to isolate the magnetic field generated by the toroid(s) in this probe within the body of the probe, that is to prevent its passing any substantial distance from the enclosure such that it not disturb other sensors or parts of process equipment which may be located near the conductivity probe. A variety of magnetic shielding methods such as, but not limited to, metallic boxes, metallic coatings or other conductive layers applied to the outside of the conductivity probe assembly can be used for this purpose.

It may also be appreciated that although only one toroid stack and one PCB shield opening are referred to in the exemplary drawings and descriptions herein, it would be possible to have side-by-side toroid/shield stacks and openings in one enclosure. This might be applicable in the case where very different designs and electronics need to be used for a "multi-fluid" or "multi-range" conductivity monitor, or in the case where several pipes are in close proximity and it is easier to have all the conductivity sensors in one housing rather than in separate housings.

Conductivity probes constructed according to the described invention can be used in any application in which prior art conductivity probes can be used, that is to say in the measurement of the conductivity of any type of fluid. Exemplary applications include, but are not limited to, water salinity monitoring, desalination process monitoring, desiccant conversion of pure water from air cycle processes, washing operations in which addition of cleaning chemicals are monitored, plating bath monitoring, measurements in control systems for chemical plants, contamination measurements in hydrocarbons, and wastewater and environmental monitoring. Particular optimization of measurement circuitry may be needed for specific applications, such as low level contamination monitoring in ultrapure water streams. The probe may be immersed in a bath or tank of fluid, or may have piping sections built into it such that fluid can flow through the central aperture.

It will be clear that the described invention is well adapted to achieve the purposes described above, as well as those inherent within. The citation of any publication is for its disclosure prior to the filing date and should not be construed as an admission that the present invention is not entitled to antedate such publication by virtue of prior invention. Numerous other changes may be made which will readily suggest themselves to those skilled in the art and which are encompassed both in the spirit of the disclosure above and the appended claims.

What is claimed is:

1. An apparatus for measuring the conductivity of fluids via noncontact means, the apparatus comprising:
   a housing, containing two or more toroids coaxially stacked along a central opening in said housing in order to form a single bore for fluid passage, at least one toroid having an input for voltage and current in order to generate a magnetic field, said magnetic field generating toroid herein referred to as a signal toroid, and at least one toroid having means for magnetic flux sensing by means of an output for voltage and current, said flux sensing toroid herein referred to as a sense toroid; and
   a magnetically transparent enclosure around said toroids; and
   means for applying an electrical current to said signal toroid in order to generate a magnetic field; and
   means for bringing a signal out from said sense toroid to indicate conductivity of a fluid; and
   at least one electrically insulating layer, each layer having a single bore for fluid passage, each layer being coaxially stacked between said toroids along said central opening in said housing, each of said insulating layers containing at least two conductive layers; and
   each conductive layer used as a separate electrical ground.

2. An apparatus as defined in claim 1, wherein a conductive loop through said central opening attached to at least two separately measurable equivalent resistors is used to provide a known resistance function for said sense toroid in order to perform calibration of said apparatus.

3. An apparatus as defined in claim 2, wherein switching between different pairs of resistors is used to calibrate said apparatus for different ranges of conductivity measurement.

4. An apparatus as defined in claim 1, wherein said conductive layer closest to said sense toroid is grounded to the virtual ground of an Analog Front End component, said virtual ground being held at a different voltage level than the power ground.

5. An apparatus as defined in claim 1, wherein said insulating layer with said conductive layers is comprised of a PCB.

6. An apparatus as defined in claim 5, wherein sensor components are mounted on or placed near and attached electrically to said PCB and used for measurement of properties relating to components of said apparatus.

7. An apparatus as defined in claim 5, wherein temperature sensor components are mounted on or placed near and attached electrically to said PCB and used for measurement of temperature of at least one of said toroids.

8. An apparatus as defined in claim 5, wherein pressure sensor components are mounted on or placed near and attached electrically to said PCB and used for measurement of pressure on said apparatus.

9. An apparatus as defined in claim 5, wherein vibration sensor components are mounted on or placed near and attached electrically to said PCB and used for measurement of vibration affecting said apparatus.

10. An apparatus as defined in claim 5, wherein magnetic field sensor components are mounted on or placed near and attached electrically to said PCB and used for measurement of said magnetic field.

11. An apparatus as defined in claim 5, wherein circuitry components are placed on and attached electrically to said PCB.

12. An apparatus as defined in claim 11, wherein said circuitry components are used for local processing of signals from said toroids.

13. An apparatus as defined in claim 11, wherein said circuitry components are used for local storage of data in memory circuitry for operation or calibration of said conductivity sensor.

14. An apparatus as defined in claim 11, wherein said circuitry components include at least one Analog Front End component which amplifies the signal from at least one of said sense toroids before the signal reaches any other circuit components.

15. An apparatus as defined in claim 11, wherein said circuitry components include at least one Analog Front End component whose virtual ground is electrically connected to said conductive layer, said virtual ground being held at a different voltage level than the power ground.

16. An apparatus as defined in claim 11 wherein said circuitry components include at least two Analog Front End components in order to take signals from said toroids and perform a differential comparison of the magnitudes of the signals.

17. An apparatus as defined in claim 11, wherein said circuitry components include at least one capacitor across the leads of each of said toroids in order to form a "tank" circuit.

18. An apparatus as defined in claim 17, wherein said "tank" circuit has a broad enough response to provide amplification of response over at least one order of magnitude of range of conductivity of said fluid without adjusting the frequency of said electrical current applied to the signal toroid.

19. An apparatus as defined in claim 11 wherein said circuitry components include, between said sense toroid and any other circuit components, either an analog to digital converter or an amplifier to raise low level signals generated by said sense toroid to higher level voltage or current signals.

20. An apparatus as defined in claim 12 wherein said circuitry components include means for transmitting signals out from said apparatus wirelessly.

21. An apparatus as defined in claim 13, wherein a conductive loop through said central opening attached to at least two separately measurable equivalent resistors is used to provide a known resistance function for said sense toroid in order to perform calibration of said apparatus.

22. An apparatus as defined in claim 21, wherein switching between different pairs of resistors is used to calibrate said apparatus for different ranges of conductivity measurement.

23. A method for measuring the conductivity of fluids via noncontact means with high sensitivity, by using a conductivity measuring cell including two or more toroids coaxially stacked along a central opening in a housing in order to form a single bore for fluid passage, a conducting electrical shield between at least two of said toroids, one of said toroids designated a signal toroid and one designated a sense toroid, a source of electrical current and two or more sets of wires, comprising the steps of:
applying said electrical current to wires wrapped around said signal toroid in order to generate a magnetic field in the fluid passage;
sensing said magnetic field using wires wrapped around said sense toroid to generate a low level electrical signal in said wires; and
shielding said signal toroid from said sense toroid by using at least two conductive layers stacked between said toroids such that each conductive layer is used as a separate ground.

24. A method as defined in claim 23, wherein shielding is achieved by grounding one or more conductive layers to the same ground as said signal toroid and by grounding one or more other conductive layers to a separate ground used by said sense toroid.

25. A method as defined in claim 23, wherein shielding is achieved by grounding one or more conductive layers to the same ground as said signal toroid, grounding one or more other conductive layer to the same ground as said sense toroid, and having one or more electrically floating conductive layers.

26. A method as defined in claim 23, wherein shielding is achieved by electrically connecting one or more of said conductive layers to a virtual ground plane of an Analog Front End circuit component, said virtual ground plane being held at a different voltage level than the power ground.

27. A method as defined in claim 23, wherein deriving a calibration function for said conductivity measuring cell is carried out by means of placing a first resistor and conductive loop into parallel electrically with the resistive fluid being measured, measuring a first equivalent resistance, then forming a second equivalent resistance by means of a second resistor, measuring a second equivalent resistance, and using these two equivalent resistance values for said derivation.

28. A method as defined in claim 23, wherein deriving a calibration function for said conductivity measuring cell is carried out by means of placing a first resistor and conductive loop into parallel electrically with the resistive fluid being measured, measuring a first equivalent resistance, then repeating this with at least two additional resistors such that at least two additional equivalent resistances are formed and used for said derivation.

29. A method for measuring the conductivity of fluids via noncontact means with high sensitivity, by using a conductivity measuring cell including two or more toroids coaxially stacked along a central opening in a housing in order to form a single bore for fluid passage, a conducting electrical shield between at least two of said toroids, one of said toroids designated a signal toroid and one designated a sense toroid, a source of electrical current and two or more sets of wires, comprising the steps of:
applying said electrical current to wires wrapped around said signal toroid in order to generate a magnetic field in the fluid passage;
sensing said magnetic field using wires wrapped around said sense toroid to generate a low level electrical signal in said wires; and
shielding said signal toroid from said sense toroid by using a PCB board having at least one conductive layer acting as a ground plane to form said conducting electrical shield.

30. A method as defined in claim 29, wherein shielding is achieved by electrically connecting one or more of said conductive layers to a virtual ground plane of an Analog Front End circuit component, said virtual ground plane being held at a different voltage level than the power ground.

31. A method as defined in claim 29, wherein deriving a calibration function for said conductivity measuring cell is carried out by means of placing a first resistor and conductive loop into parallel electrically with the resistive fluid being measured, measuring a first equivalent resistance, then forming a second equivalent resistance by means of a second resistor, measuring a second equivalent resistance, and using these two equivalent resistance values for said derivation.

32. A method as defined in claim 29, wherein deriving a calibration function for said conductivity measuring cell is carried out by means of placing a first resistor and conductive loop into parallel electrically with the resistive fluid being measured, measuring a first equivalent resistance, then repeating this with at least two additional resistors such that at least two additional equivalent resistances are formed and used for said derivation.

33. A method as defined in claim 29, wherein grounding of circuit components mounted on said PCB board uses at least one of the same conductive layers as shielding between said toroids.

34. A method as defined in claim 33, wherein comparing outputs of said circuit components comprising Analog Front End type devices which outputs are derived from signals obtained from said toroids is used to make a differential comparison of signal magnitudes in order to obtain greater circuit stability.

35. A method as defined in claim 33, wherein, before the signal reaches any other circuit components, either amplifying low level signals generated by said sense toroid to higher level voltage or current signals is carried out, or converting low level signals to digital signals is carried out.

36. A method as defined in claim 33, wherein converting said low level electrical signals generated by said sense toroid to wireless signals is carried out.

37. A method as defined in claim 33, wherein monitoring of the temperature of said circuit components is carried out.

38. A method as defined in claim 37, wherein monitoring of the temperature of at least one of said toroids is carried out.

39. A method as defined in claim 33, wherein measuring said magnetic field is performed with at least one magnetic sensor component mounted on or placed near and attached electrically to said PCB.

40. A method as defined in claim 33, wherein placing one or more capacitors across the leads of said toroids in order to create a "tank circuit" creates a resonant circuit using said toroids and said capacitor(s) in order to improve signal response in said conductivity measuring cell.

41. A method as defined in claim 40, wherein amplifying said response using said "tank" circuit is providing amplification of response over at least one order of magnitude of range of conductivity of said fluid without adjusting the frequency of said electrical current applied to the signal toroid.

* * * * *